United States Patent
Lee et al.

(10) Patent No.: US 11,648,706 B2
(45) Date of Patent: May 16, 2023

(54) SELECTIVE SINTER-BASED FABRICATION OF FULLY DENSE COMPLEXING SHAPED PARTS

(71) Applicant: San Diego State University, San Diego, CA (US)

(72) Inventors: Geuntak Lee, Seoul (KR); Eugene Olevsky, San Diego, CA (US); Charles Maniere, Toulouse (FR)

(73) Assignee: San Diego State University Research Foundation, San Diego, CA (US)

( * ) Notice: Subject to any disclaimer, the term of this patent is extended or adjusted under 35 U.S.C. 154(b) by 444 days.

(21) Appl. No.: 17/050,835

(22) PCT Filed: Apr. 26, 2019

(86) PCT No.: PCT/US2019/029508
§ 371 (c)(1),
(2) Date: Oct. 26, 2020

(87) PCT Pub. No.: WO2019/210285
PCT Pub. Date: Oct. 31, 2019

(65) Prior Publication Data
US 2021/0229315 A1    Jul. 29, 2021

Related U.S. Application Data

(60) Provisional application No. 62/662,762, filed on Apr. 26, 2018.

(51) Int. Cl.
*B28B 7/34* (2006.01)
*B33Y 10/00* (2015.01)
(Continued)

(52) U.S. Cl.
CPC ................ *B28B 7/342* (2013.01); *A61C 5/77* (2017.02); *B22F 3/04* (2013.01); *B28B 1/001* (2013.01);
(Continued)

(58) Field of Classification Search
None
See application file for complete search history.

(56) References Cited

U.S. PATENT DOCUMENTS 7,658,762 B2  2/2010 Lashinski et al.
8,096,224 B2  1/2012 Martin et al.
(Continued)

*Primary Examiner* — Mohammad M Ameen
(74) *Attorney, Agent, or Firm* — Juneau & Mitchell; Todd L. Juneau

(57) ABSTRACT

The invention relates to a process for fabricating complex mechanical shapes from metal or ceramic, and in particular to fabricating complex mechanical shapes using a pressure-assisted sintering technique to address problems relating to variations in specimen thickness and tooling, or densification gradients, by 3-D printing of a sacrificial, self-destructing powder mold is created using e.g. alumina and swellable binders such as polysaccharides. The binder-free sintering powder that forms the manufactured item is injected into the mold, and high pressure is applied. The powder assembly can then be sintered by any pressure assisted technique to full densification and the self-destructing mold allows the release of the fully densified complex manufactured item.

14 Claims, 3 Drawing Sheets

Schematics of fabrication process using self-destructible powdery mold

(51) Int. Cl.
*B33Y 80/00* (2015.01)
*A61C 5/77* (2017.01)
*B33Y 70/10* (2020.01)
*B22F 3/04* (2006.01)
*B28B 1/00* (2006.01)
*C04B 35/10* (2006.01)
*C04B 35/48* (2006.01)
*C04B 35/645* (2006.01)

(52) U.S. Cl.
CPC .............. *B28B 7/346* (2013.01); *B33Y 10/00* (2014.12); *B33Y 70/10* (2020.01); *B33Y 80/00* (2014.12); *C04B 35/10* (2013.01); *C04B 35/48* (2013.01); *C04B 35/6455* (2013.01); *C04B 2235/3217* (2013.01); *C04B 2235/3244* (2013.01); *C04B 2235/3246* (2013.01); *C04B 2235/6026* (2013.01); *C04B 2235/6562* (2013.01); *C04B 2235/6567* (2013.01)

(56) References Cited

U.S. PATENT DOCUMENTS

| | | |
|---|---|---|
| 8,568,897 B2 | 10/2013 | Ganley et al. |
| RE44,820 E | 4/2014 | Ying et al. |
| 8,796,166 B2 | 8/2014 | Holand et al. |
| 8,828,311 B2 | 9/2014 | Medina et al. |
| 8,883,250 B2 | 11/2014 | Miller et al. |
| 8,940,220 B2 | 1/2015 | Raj et al. |
| 9,005,420 B2 | 4/2015 | Tomantschger et al. |
| 9,315,663 B2 | 4/2016 | Appleby et al. |
| 9,364,896 B2 | 6/2016 | Christensen et al. |
| 9,512,544 B2 | 12/2016 | Heikkila |
| 9,533,077 B2 | 1/2017 | James et al. |
| 9,636,229 B2 | 5/2017 | Lang et al. |
| 9,713,860 B2 | 7/2017 | Chaumat et al. |
| 10,166,316 B2 | 1/2019 | Landon et al. |
| 10,226,313 B2 | 3/2019 | Jung et al. |
| 10,273,567 B2 | 4/2019 | Isaac |
| 10,395,372 B2 | 8/2019 | Anand et al. |
| 10,571,642 B1 | 2/2020 | Cohen et al. |
| 10,610,460 B2 | 4/2020 | Brodkin et al. |
| 10,737,984 B2 | 8/2020 | Schaedler et al. |
| 10,780,501 B2 | 9/2020 | Wu et al. |
| 10,921,782 B2 | 2/2021 | Mehr et al. |
| 2008/0274351 A1* | 11/2008 | Itoh .................. C04B 35/457 425/436 R |
| 2014/0250677 A1 | 9/2014 | Lang |
| 2014/0363327 A1 | 12/2014 | Holcomb |
| 2015/0118648 A1* | 4/2015 | Johannes ............... C04B 35/48 433/199.1 |
| 2016/0015483 A1 | 1/2016 | Kumar et al. |
| 2016/0090516 A1 | 3/2016 | Yener et al. |
| 2016/0175929 A1 | 6/2016 | Colin et al. |
| 2016/0179064 A1 | 6/2016 | Arthur et al. |
| 2016/0198576 A1 | 7/2016 | Lewis et al. |
| 2016/0246908 A1 | 8/2016 | Komzsik |
| 2017/0014169 A1 | 1/2017 | Dean et al. |
| 2017/0021425 A1 | 1/2017 | Fang et al. |
| 2017/0050293 A1 | 2/2017 | Gaeta et al. |
| 2017/0239723 A1 | 8/2017 | Hoyt et al. |
| 2018/0009032 A1* | 1/2018 | Kelkar ................... B22F 5/10 |
| 2018/0009718 A1 | 1/2018 | Dichiara, Jr. et al. |
| 2018/0015674 A1 | 1/2018 | Page |
| 2018/0154574 A1 | 6/2018 | Mark |
| 2018/0221950 A1 | 8/2018 | Mark |
| 2018/0250746 A1 | 9/2018 | Symeonidis et al. |
| 2018/0272460 A1 | 9/2018 | Nelson et al. |
| 2018/0318922 A1 | 11/2018 | Valls Anglés |
| 2019/0060997 A1 | 2/2019 | Gibson et al. |
| 2019/0344331 A1 | 11/2019 | Bewlay et al. |
| 2019/0388128 A1 | 12/2019 | Wilson et al. |
| 2020/0063242 A1 | 2/2020 | Valls Anglés |
| 2020/0217206 A1 | 7/2020 | Nissen et al. |
| 2021/0002744 A1 | 1/2021 | Martin et al. |
| 2021/0138737 A1 | 5/2021 | Tibbits et al. |

* cited by examiner

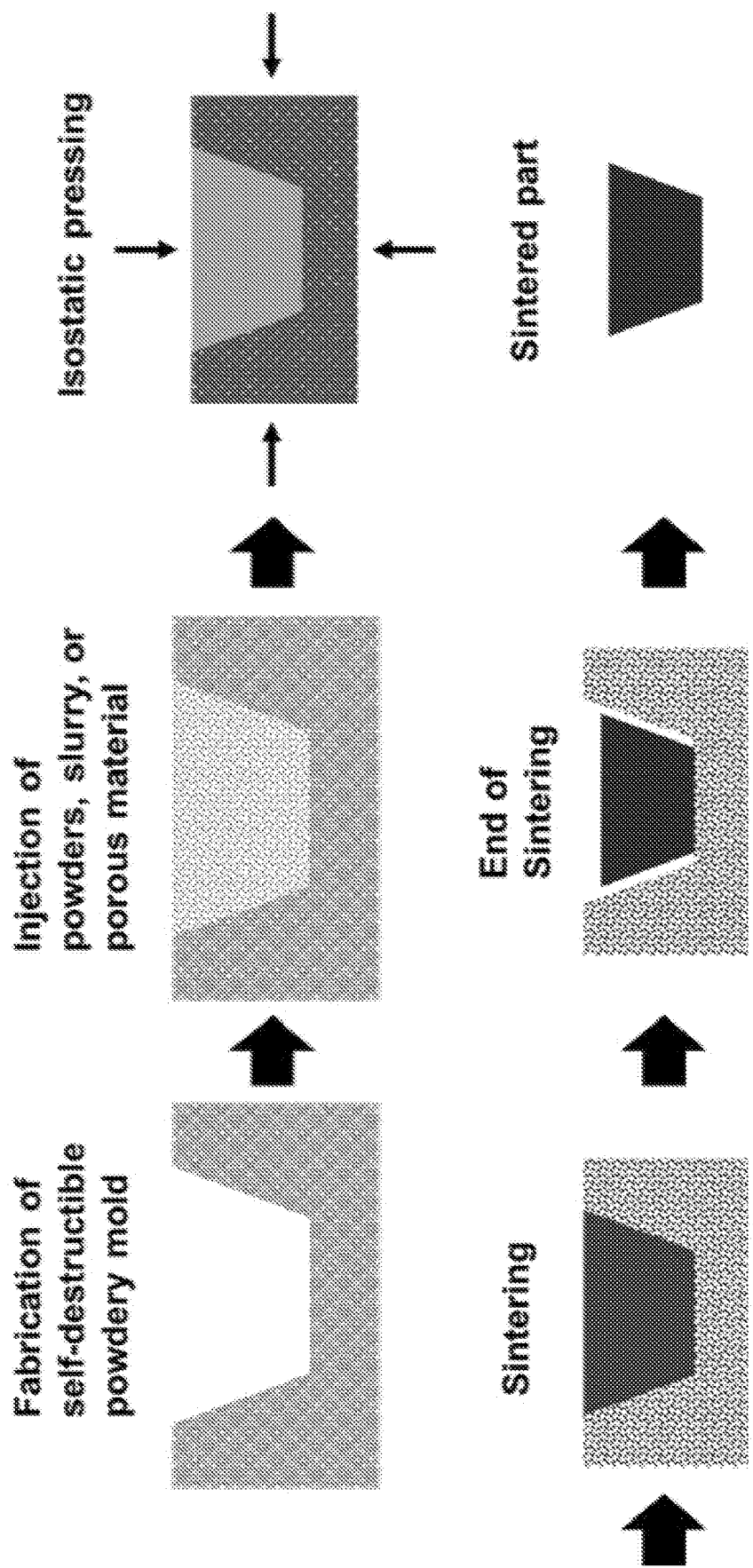
Figure 1. Schematics of fabrication process using self-destructible powdery mold

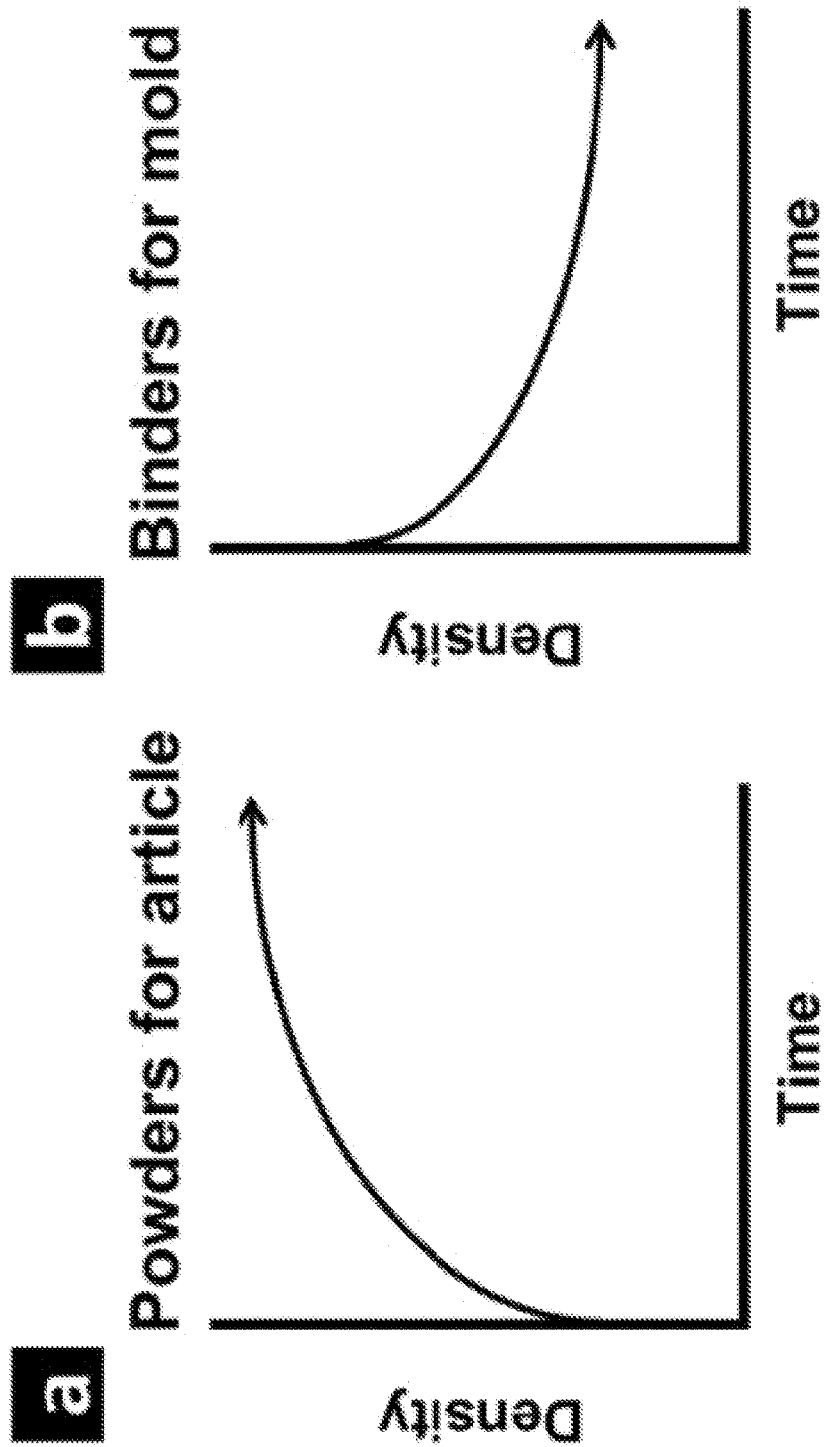
Figure 2. Densification behavior of (a) article powders and (b) binders in sacrificial mold

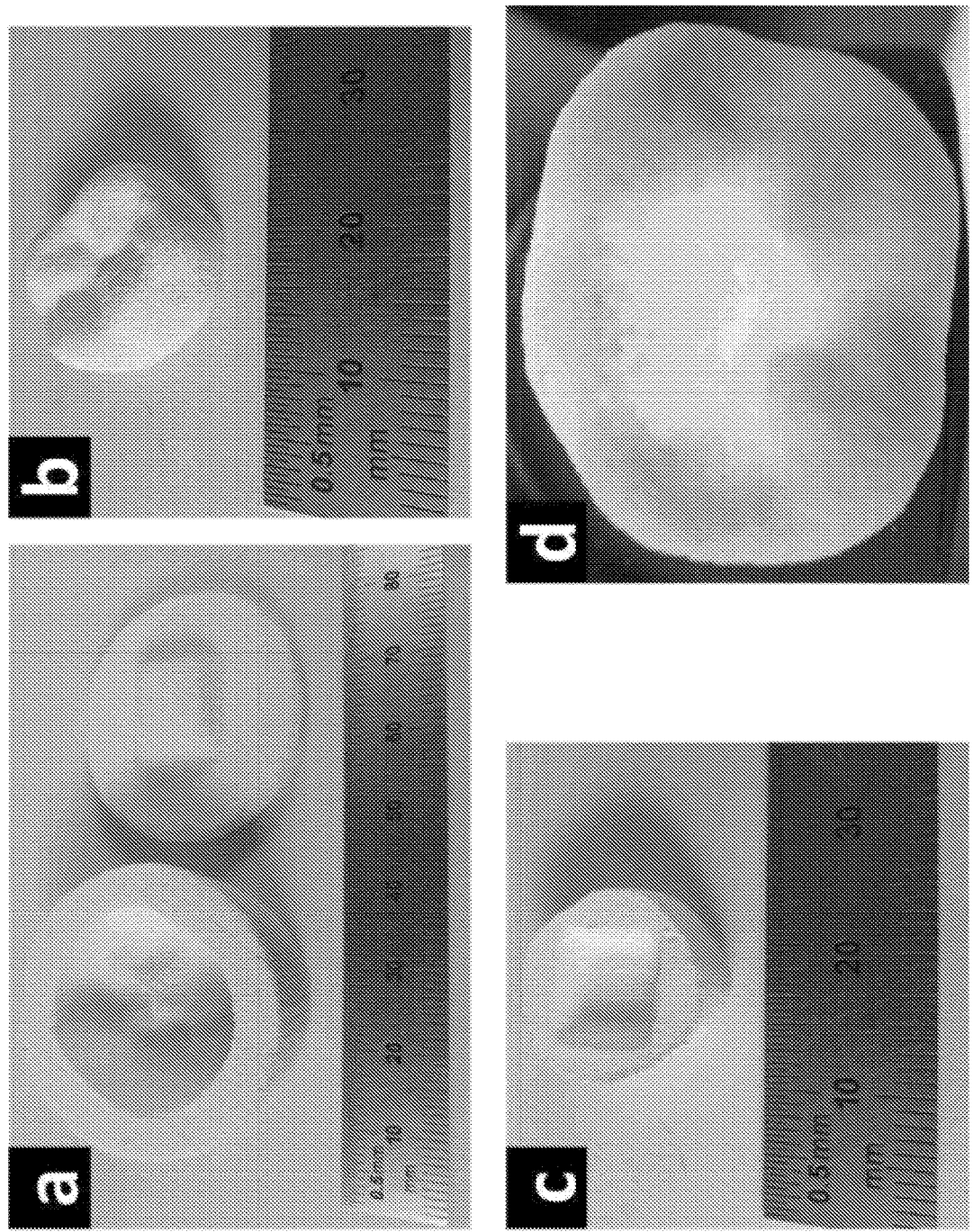
Figure 3. (a) Sacrificial powdery mold and cap. Dental crown (Translucent zirconia) made with this method, (b) top, (c) bottom and (d) transluceney test with green laser

SELECTIVE SINTER-BASED FABRICATION OF FULLY DENSE COMPLEXING SHAPED PARTS

STATEMENT REGARDING FEDERALLY SPONSORED R&D

The invention was made with U.S. Government support under Contract No. DE-SC0008581 awarded by the U.S. Dept. of Energy. The U.S. Government has certain rights in the invention.

CROSS-REFERENCE TO RELATED APPLICATIONS

Provided per USPTO rules by Application Data Sheet.

NAMES OF PARTIES TO JOINT RESEARCH AGREEMENT

Provided per USPTO rules by Application Data Sheet.

REFERENCE TO SEQUENCE LISTING

Provided per USPTO rules by Application Data Sheet.

STATEMENT RE PRIOR DISCLOSURES

Provided per USPTO rules by Application Data Sheet.

BACKGROUND OF THE INVENTION

Field of the Invention

The invention relates to a process for fabricating complex mechanical shapes from metal, metal-alloy, or ceramic, and in particular to fabricating complex mechanical shapes using a pressure-assisted sintering technique to address problems relating to variations in specimen thickness and tooling, or densification gradients, by 3-D printing of a sacrificial, self-destructing powder mold is created using e.g. alumina and swellable binders such as polysaccharides. The binder-free sintering powder that forms the manufactured item is injected into the mold, and high pressure is applied. The powder assembly can then be sintered by any pressure assisted technique to full densification and the self-destructing mold allows the release of the fully densified complex manufactured item.

DESCRIPTION OF THE RELATED ART

The advanced pressure assisted sintering techniques such as spark plasma sintering, which involves high pressures (up to 100 MPa) and very high temperatures (up to 2500° C.), enable the consolidation of nearly all the powders from polymers to high temperature materials (such as silicon carbide) with the possibility to control the microstructure. These techniques are very useful for the fabrication of high performance materials, but their main drawback are the difficulties to generate complex shapes. In most of these processes a certain level of post-processing porosity remains, when complex shapes' fabrication is attempted, due to the high complexity of the tooling involved in the production of these shapes.

BRIEF SUMMARY OF THE INVENTION

To address this problem a general approach involving a method to make fully dense metal and ceramic complex shape components is developed.

This method can generate highly complex shape components using integration of the advanced complex shapes methods of 3D printing and the high quality of the material microstructures obtained by the pressure assisted sintering techniques.

In this approach, a very high complex shape is generated by 3D printing (or other polymer manufacturing techniques) and a sacrificial, self-destructing powder mold is created using e.g. alumina and swellable binders such as polysaccharides. The binder-free sintering powder that forms the manufactured item is injected into the mold, and high pressure is applied. The powder assembly can then be sintered by any pressure assisted technique to full densification and the graphite interface (inert) allows the release of the internal fully densified complex shape part.

In a preferred embodiment, the invention provides in a non-limiting aspect a process for producing a sintered powder manufactured item, comprising the steps:

STEP 1—preparing a sacrificial powder mold of a manufactured item, the sacrificial powder mold made using 3D printing and the sacrificial powder of the sacrificial powder mold consisting of a high-temperature sintering powder and a swellable binder to create a self-destructable sacrificial powder mold when sintered;

STEP 2—loading a powder sintering material into the sacrificial powder mold to create a powder-mold assembly, wherein the powder sintering material is substantially free of binder;

STEP 3—applying isostatic pressure to the powder-mold assembly;

STEP 4—sintering of the powder-mold assembly; and

STEP 5—obtaining a sintered-powder cast manufactured item from the self-destructed sintered sacrificial powder mold.

In another preferred embodiment, the invention provides in a non-limiting aspect a method consisting of:

STEP 1—preparing a sacrificial powder mold of a dental crown, the sacrificial powder mold made using 3D printing and the sacrificial powder of the sacrificial powder mold consisting of a high-temperature alumina sintering powder and at least one swellable binder to create a self-destructable sacrificial powder mold when sintered;

STEP 2—loading a zirconia powder sintering material into the sacrificial powder mold to create a powder-mold assembly, wherein the powder sintering material is substantially free of binder;

STEP 3—applying isostatic (high) pressure to the powder-mold assembly;

STEP 4—sintering of the powder-mold assembly in a tube furnace; and

STEP 5—obtaining a sintered-powder cast zirconia dental crown from the self-destructed sintered sacrificial powder mold, wherein the relative density of the dental crown is ~99.42%.

In another preferred embodiment, the invention provides in a non-limiting aspect wherein the powder sintering material of STEP 2 is metal or ceramic. In another preferred embodiment, the invention provides in a non-limiting aspect wherein the isostatic pressure of STEP 3 is at least 400 MPa.

In another preferred embodiment, the invention provides in a non-limiting aspect wherein the sintering of STEP 3 is at 1400 degrees Celsius for 4 hours under a heating rate of 3 degrees Celsius/minute.

In another preferred embodiment, the invention provides in a non-limiting aspect wherein the loading of STEP 2 includes a preliminary step of coating the sacrificial powder mold with a graphite spray.

In another preferred embodiment, the invention provides in a non-limiting aspect wherein the high-temperature sintering powder of STEP 1 is alumina, and the swellable binder of STEP 1 is selected from the group consisting of a polysaccharide, a mono-saccharide, a di-saccharide, a tri-saccharide, a starch, a carbohydrate, a saccharide derivative, and a mixtures and a combination thereof.

In another preferred embodiment, the invention provides in a non-limiting aspect wherein the zirconia powder sintering material is a 3 mol % yttria-stabilized zirconia powder.

In another preferred embodiment, the invention provides in a non-limiting aspect wherein the sacrificial powder mold of STEP 1 consists of 74% alumina, 13% powdered sugar and 13% maltodextrin.

In another preferred embodiment, the invention provides in a non-limiting aspect a method consisting of:

1) generating a polymer graphite skeleton by 3D printing or other methods;

2) surrounding of this rigid or semi-rigid polymer skeleton, wherein the skeleton can have a highly complex geometry, by the powder of the material(s) to be formed, wherein the powder of the sacrificial area can be different from the powder of the main part;

3) transforming this assembly of powder/polymer into a pure powders assembly by a heat treatment under vacuum or oxygen/hydrogen free atmosphere enabling the controlled degradation of the polymer interface into a graphite powder interface that does not sinter; and 4) after sintering, releasing the internal complex parts.

In another preferred embodiment, the invention provides in a non-limiting aspect wherein the polymer shell model or polymer skeleton can be coated by an inner ceramic powder to prevent eventual undesired carbonization reaction between the graphite powder and the main part powders.

In another preferred embodiment, the invention provides in a non-limiting aspect wherein the polymer interface degradation can be in situ incorporated in the sintering process with a simple pre-heating, which allows a one-step complex shaping process.

In another preferred embodiment, the invention provides in a non-limiting aspect wherein the polymer shell model or the polymer skeleton can be designed for a simultaneous multiple parts sintering.

BRIEF DESCRIPTION OF THE SEVERAL VIEWS OF DRAWING

FIG. 1 is an illustrated process flowchart showing a non-limiting preferred embodiment of the STEPS of the inventive method.

FIG. 2 is a two-part density graph showing aspects of a non-limiting preferred embodiment of the STEPS of the inventive method.

FIG. 3 is a series of photographic images showing a non-limiting embodiment of the method of the invention illustrating manufacture of a dental crown manufactured item.

DETAILED DESCRIPTION OF THE INVENTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Many modifications and variations can be made without departing from its spirit and scope, as will be apparent to those skilled in the art.

Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

FIGURES

This approach provides a novel method to make fully dense metal and ceramic complex shape components. Known additive manufacturing technologies producing complex shape components using binders, include the complex and time-consuming debinding process and render low green density products. Using the proposed combination of selective sintering and 3D printing technology, fully dense complex parts can be easily produced.

Referring now to the Figures, FIG. 1 illustrates one preferred embodiment wherein the total process is composed of the following steps: 1. Fabrication of sacrificial powder mold, 2. Injection of powders or slurry to the mold, 3. Isostatic pressing of the sacrificial mold and powder assembly, and 4. Sintering, as shown in FIG. 1.

Referring now to FIG. 2, here, the sacrificial powder mold, made from powders with high sintering temperature and binder can be made using a regular AM method such as the binder jetting method. This sacrificial mold performs 3 consecutive functions in the complex shape fabrication process: 1. Shaping of the complex part by pouring the powders or slurry into the mold, 2. Pressure transmission during isostatic pressing to increase the green density of the article prior to sintering, and 3. Self-destruction during sintering by using the binder which swells during heating (FIG. 2).

Generally, nanopowders cannot be used to make the parts produced by the general binder jetting method due to their low flowability. Due to the controllable density of the sacrificial powder mold utilized in the present method, nanopowders can be used as the article's material, resulting in the reduction of the sintering temperature and grain size of the final complex parts, which is not possible when using other additive manufacturing methods.

Also, the articles fabricated by binder jetting methods have binders inside their volume; therefore pressure-assisted consolidation technologies, which can increase the density of complex parts significantly, cannot be applied, otherwise the binder inside of the article generates the shape distortion or cracks during the sintering process. However, in the present invention, the article material can include pure powders without binders; hence the pressure can be applied without any problem.

This invention can be easily industrially implemented since it doesn't require cost- and time-consuming steps like curing, debinding and infiltration which are generally used by the binder jetting technology. Also, mass production is possible because this method doesn't require any external pressure assistance, which usually adds complexity to the fabrication process.

FIG. 3 provides a non-limiting example of preparing a dental crown made of zirconia that has been fabricated using this approach. The sacrificial powder mold and cap were made of alumina and binders, as shown in FIG. 3(a). After injection of zirconia powder into the mold, high pressure has been applied to the mold and zirconia powder assembly together. Pressed assembly was directly transferred to a tube furnace for sintering. The final dental crown obtained is shown in FIGS. 3(b) and (c). The level of translucency is confirmed by a laser test in FIG. 3(d), indicating that this method can provide high-density products with small average grain size structure. The relative density of the manufactured dental crown is ~99.42% which is not achievable by the regular binder jetting approach.

TECHNICAL DESCRIPTION

A novel approach to make fully dense net-shaped materials has been developed. Fabrication of fully dense complex shape ceramic parts is a major challenge of additive manufacturing (AM) technology. The selective laser melting (SLM) or selective laser sintering (SLS) utilizing high power laser treatment of materials, generate thermal shock conditions during manufacturing, producing cracks in the fabricated parts, which often become a reason of low mechanical strength. The slurry based 3D printing technologies use organic or inorganic binders to glue the powders particles to each other for making complex shape parts. The "negative" AM technology, which employs a polymer mold to make complex shape parts, also uses ceramic slurry with binders. However, after producing a green specimen by slurry-based technique, the complex and time-consuming debinding process becomes unavoidable. Sometimes it takes a few days to remove the binders from the part with a thick shell made by the slurry based methods. Also, after the debinding step, some binder elements may remain in the specimen's volume and generate gas pressure during sintering, which impedes the sintering process resulting in low relative density and adversely affecting the mechanical properties of the final products.

In order to get fully dense complex part made of ceramic or metal, we introduce selective sintering-based fabrication of fully dense complex shaped parts. The schematics of total fabrication process of this invention are shown in FIG. 1. First, a sacrificial mold, which can be 3D printed, is made from the mixed powders (Component 1: ceramic powders, which have higher sintering temperature compared with the article powders and Component 2: binder powders providing swelling during heating). The concept of consolidation/desintering used in this invention is shown in FIG. 2. During sintering, the article powders are densified and shrink in volume, while binder powders in the sacrificial mold swell in volume. The surface of the sacrificial powder mold can be coated with the spray of high-temperature material such as carbon and boron nitride to block the possible reaction between the article powder and the sacrificial mold. Secondly, the cavity of the sacrificial powder mold can be filled with the article powders, slurry or other porous materials, and then the mold is closed with a cap made from the same powder as the mold. Thirdly, the isostatic pressing methods like cold isostatic pressing (CIP) or warm isostatic pressing (WIP) are applied to densify the article parts and the sacrificial powder mold at the same time. By matching the density of the sacrificial powder mold and article powders, possible shape distortions during isostatic pressing can be limited. After pressing, without removing the mold and without the need for debinding, both the powder mold and the article powders are sintered in a regular sintering furnace without pressure application. During the sintering process, the article is consolidated into a complex shape. At the same time, the powder mold can be easily removed due to 3 reasons: 1. The sintering temperature of the powder used in the mold is higher than that of the article powder 2. The binder used in the mold swells during the heating, which makes a mold to automatically collapse (self-destruct). 3. High-temperature powder spray blocks the reaction between the article powders and the powder used in the sacrificial mold. Therefore, the complex part can be obtained right after sintering without the need for a break of the sacrificial mold which may harm the sintered article.

A regular binder jetting process produces 3D shape components with low green density, which prevents the densification during the follow-up sintering due to the presence of macroporosity in the green specimen. Also, the articles fabricated by binder jetting have binders inside their volume; therefore pressure-assisted consolidation technologies cannot be applied, otherwise the binder inside of the article generates the shape distortion or cracks during the sintering process.

However, in the present invention, the article material can include pure powders without binders; hence the pressure can be applied without any problem. By pressing the sacrificial mold and the article powder at the same time, the green density of the processed part can be increased to the level higher than 50%, so that it is ready to be consolidated during sintering to achieve full density under the optimum temperature setting.

In addition, this approach enables the usage of nanopowders, which are typically not utilized in regular binder jetting processes due to their limited flowability, thereby rendering lower sintering temperatures and smaller average grain sizes of the final complex parts, which was not achievable by any AM method before.

There is one more advantage to this invention regarding the productivity. This invention enables the avoidance of the use of the pressure-assisted sintering, which otherwise generally adds complexity to mass production. Thereby many parts with different or same complex shapes can be obtained by three-step processing only: powdery mold fabrication, isostatic pressing step and the following sintering step. (No need of curing, debinding and infiltration which are generally used in the binder jetting technology) Referring again to FIG. 3, the non-limiting example explains that a dental crown made from the 3 mol % yttria-stabilized zirconia powders (Z-pex Smile, Tosoh, Inc., Japan) has been fabricated using this approach. The sacrificial powder mold and cap were made of 74% alumina, 13% powdered sugar and 13% maltodextrin, as shown in FIG. 3(a). After coating the sacrificial mold with graphite spray, zirconia powders were poured into it and closed with the cap. Next, 400 MPa pressure was applied to the whole assembly under CIP. Pressed assembly was directly transferred to a tube furnace and sintered at 1400° C. for 4 hours under a heating rate of 3° C./min. The final dental crown obtained is shown in FIGS. 3(b) and (c). The level of translucency is confirmed by a laser test in FIG. 3(d), indicating that this method can provide high-density products with a small average grain size structure. The relative density of the manufactured dental crown is ~99.42% which cannot be obtained by the regular binder jetting approach.

Advantages

Advantages of this approach are that the invented process uses a swelling binder as a material component of the sacrificial powder mold. The mold utilized in the current invention uses the binder, which swells during heating; this event is usually attempted to be avoided in additive manufacturing techniques, such as binder jetting and ceramic injection molding, since it causes complications during the follow-up sintering.

Most of the binder-assisted additive manufacturing studies are focused on the optimization of the binder materials or on increasing the green density of the complex shape parts. The former one includes the synthesis of binders, which can be easily removed during heating, and the optimization of the debinding process by controlling the heating profile. The latter one includes the optimization of the composition of the binder—article powder system and the optimization of the article powder size distributions. In the described invention, however, the swelling of the used binders helps removing the sacrificial mold naturally during the sintering process (due to its self-destruction.)

Another critical advantage of the invented process lies in its time, cost efficiency and simplicity. This invention doesn't require the time-consuming or sometimes impossible debinding process. Also, the simultaneous de-molding (mold self-destruction) and sintering of the article without the debinding process during the heating step save the time and energy spent. Indeed, some prototypes of almost fully dense complex ceramic zirconia dental crowns have already been fabricated and are shown in FIG. 3.

Example

A dental crown made from the 2-5 mol % dental article powders selected from Zirconia, Lithium Disilicate, Leucite, Alumina, Spinel, Alumina-Zirconia, Fluorapatite, Sanidine (potassium feldspar—$K(AlSi_3O_8)$) is fabricated using this approach. A sacrificial powder mold and cap were made of 60-80% alumina, 20-40% carbohydrate. After coating the sacrificial mold with graphite or boron spray, article powder (s) are poured into the mold and closed with the cap. Next, 300-500 MPa pressure was applied to the whole assembly under cold or warm isostatic pressing (CIP or WIP). The pressed assembly is directly transferred to a tube furnace and sintered at 1000-1800° C. for 3-9 hours under a heating rate of 3-10° C./min. The final dental crown obtained is expected as a high-density product with a small average grain size structure, with a relative density of the manufactured dental crown from 90%-99.9%.

Example

A powder-form manufactured part is made from the 2-5 mol % article powders selected from the powders and/or nanopowders listed herein. A sacrificial powder mold and cap were made of 60-80% alumina, 20-40% carbohydrate. After coating the sacrificial mold with graphite or boron spray, the article powder(s) are poured into the mold and closed with the cap. Next, 70-800 MPa pressure was applied to the whole assembly under cold or warm isostatic pressing (CIP or WIP). The pressed assembly is directly transferred to a tube furnace and sintered at 0.5 to 0.9 of the article powder's melting point, or alternatively from 500-1800° C., for an sintering appropriate to the article powder, or alternatively to control carburization, oxidation, unwanted reactions, and additives, or alternatively from 10 minutes up to 10 hours under a heating rate of 3-10° C./min. The final powder-form manufactured part obtained is expected as a high-density product with a small average grain size structure, with a relative density of the manufactured part from 90%-99.9%.

Example—Sinter Temps

METAL/MATERIAL SINTERING TEMP deg. C. MELTING PT.
Al—Al2O3 composite 500-600 660.3
Al—Mg alloy -0.6 of m.p. 437
Aluminum alloys 590-620 deg. C.
Brass 850-950
Bronze 740-780
Cobalt 900-1200 1495
Cu—Mg -0.6 of m.p. 485
Cu—Mn -0.6 of m.p. 870
Cu—Ti -0.6 of m.p. 860
Cu—Zr -0.6 of m.p. (-588) 980
Ferrites 1200-1500
Fe—Cu 1121
Fe—Ni 1121
Iron -0.6 of m.p. 1538
Magnesium -0.6 of m.p. 651
Molybdenum 2050 2623
Mo—Nb alloy -0.6 of m.p. 2297
Neobium -0.6 of m.p. 2477
Nickel 1000-1150
Platinum -0.6 of m.p. 1768
Silicon -0.6 of m.p. 1414
Silver 700-900 961.8
Stainless Steels 1100-1290
Tantalum 2400
Titanium -0.6 of m.p. 1688
Tungsten 2350 3422
Tungsten carbide 1100, 1430-1500
Additional Melting Points Additional melting points of metals, alloys, and materials may be found on the American Elements website, https://www.americanelements.com, for example for Lithium Titanate, https://www.americanelements.com/lithium-titanate-spinel-nanoparticles-nanopowder-12031-95-7.

EXAMPLE

Example—Differing Particle Size Vs. Temp

The densification rate changes with particle size. This can be formulated as a sintering temperature change based on particle size:

$$\ln(D2/D1) = Q/3R[1/T1 - 1/T2]$$

where R is the gas constant, T1 is the sintering temperature for particle size D1, and T2 is the sintering temperature for equivalent sintering for particle size D2. The parameter Q is the activation energy. Where sintering is measured by density, then Q is usually the grain boundary diffusion activation energy. This formula explains that the sintering temperature can change with particle size reduction.

As used herein, "nanopowder" refers to particles of metal having an average particle size of less than about 100 nanometers and an aspect ratio between one and one million. In some embodiments, a nanopowder may have an average particle size of less than 75 nm. In some embodiments, a nanopowder may have an average particle size of less than 50 nm. In some embodiments, a nanopowder has an average particle size of less than 25 nm. In some embodiments, a nanopowder may have an average particle size of less than 10 nm.

Powder and nanopowder compositions herein include, but are not limited to powder having the formula:

$$M_jX_p (\text{Powder/Nanopowder Formula})$$

wherein Mj is a positive ion or several positive ions selected from alkali metal, alkaline earth metal or transition metal; and Xp is a monoatomic or a polyatomic anion selected from Groups IIIA, IVA, VA, VIA or VIIA The term sintering is defined as the act of consolidating powder into a dense shape. The powder being sintered must additionally not melt to a great extent, some melting of secondary phases in the powder, or surface melting is allowed under this definition. If the material completely melts, the process is referred to as fusion casting. Traditionally, sintering, both pressureless and with pressure, or hot pressing, requires solid, liquid or gas material transport to consolidate an aggregate of loose powder particles into a dense shape. As used herein, the invention is not performed under pressure, and densification is performed as described herein. Sintering as used herein includes a range of 30-90% of the melting temperature of the powder material. The temperature will necessarily depend on the sintering time and the particle size. In one preferred embodiment, the sintering temperature is 30-60% of the melting temperature of the powder material. In another preferred embodiment, the sintering temperature is 50-66% of the melting temperature of the powder material. In yet another preferred embodiment, the sintering temperature is 70-90% of the melting temperature of the powder material.

Spinel (magnesium aluminate) may be used herein as a powder or as a nanopowder. Spinel is defined as a crystalline structure of the type AB2O4 where A is a 2+ cation occupying tetrahedral lattice site in an oxygen cubic close packed structure and B is a 3+ cation occupying octahedral lattice site. In a preferred embodiment, spinel is MgAL2O4 consisting of an oxide of magnesium and aluminum. Spinel powder can be prepared by wet chemistry, solid state diffusion of oxides or calcination. Spinel powder particles consist of crystallites which are less than 500 nm in size that can also be agglomerated into larger sizes varying from 500 nm to 100 μm, more typically 1-50 μm. Spinel high melting point (2135 deg. C.), high mechanical strength (150-300 MPa), is transparent from visible to 5.5 μm wavelength, and its mechanical properties are several times greater than that of glass and make it useful for a transparent armor and window material.

Powders and nanopowders are both contemplated as within the scope of the invention. Powders include particles having a mean diameter of 1 micrometer or greater. In a preferred embodiment, the powders range from 3-100 micrometers. In another preferred embodiment, the powders range from 10-500 micrometers. In yet another preferred embodiment, the powders range from 100-1000 micrometers. Nanopowders include powder particles having a mean diameter of 999 nm or less. In a preferred embodiment, the nanopowders range from 100-500 nanometers. In another preferred embodiment, the nanopowders range from 50-250 nanometers.

Powders and nanopowders contemplated as within the scope of the invention include but are not limited to powders and nanopowders comprising:
alumina and alumina composite or alloy powders and nanopowders;

barium titanate (BaTiO3) powders and nanopowders;
calcium phosphate powders and nanopowders for medical applications like bone implants;
Cerium oxide powders and nanopowders;
cobalt alloy (CoCrFeNiAl) powders and nanopowders;
copper and copper composite powders and nanopowders;
copper titanium carbide powders and nanopowders;
ferrites, iron, iron alloy powders and nanopowders;
lanthanum and lanthanum composite powders and nanopowders;
lead zirconate titanate powders and nanopowders;
lead zirconate niobate (Zn1/3Nb2/3)O3 powders and nanopowders;
lithium metal oxide powders and nanopowders such as LiNi1−xCoyMαM'βO2 where M is Ti or Zr and M' is Mg, Ca, Sr, Ba, and combinations thereof, including lithium cobalt oxide, lithium nickel oxide, lithium manganese oxide and the doped lithium metal oxides of this type, mixed lithium metal oxides of said metals and the doped derivatives, lithium iron phosphate and the doped lithium iron phosphates as well as other lithium metal phosphates, lithium titanates and other materials for the storage batteries;
magnesium and magnesium composite powders and nanopowders;
molybdenum powders and nanopowders;
Neodymium-Iron-Boron (NdFeB) powders and nanopowders for magnets and electronics;
nickel and nickel composite powders and nanopowders;
nickel alumina (Ni3Al) powders and nanopowders;
nickel-chromium-iron alloy powders and nanopowders;
nickel tantalate (NiTaO3) powders and nanopowders;
nickel titanium powders and nanopowders;
nickel-Zn-Ferrite powders and nanopowders;
Platinum alloy (Pt—Ir, Pt—Co, Pt—Pd, Pt—Ru, Pt—Au, Pt—W, Pt—Cu) powders and nanopowders;
Silicon nitride (Si3N4) powders and nanopowders;
Silicon carbide (SiC) powders and nanopowders;
Silicon composite ceramic Si3N4/SiC powders and nanopowders;
silver and silver composite powders and nanopowders;
sodium niobate (NaNbO3) powders and nanopowders;
tin and tin alloy powders and nanopowders;
Titanium alloy (TiAlSn, TiAlVn) powders and nanopowders;
Tungsten carbide powders and nanopowders; and
Tungsten carbide/cobalt powders and nanopowders.
ytterbium and ytterbium composite powders and nanopowders; and
yttrium alumina oxide (Y3/Al5/O12)(YAG) powders and nanopowders.

The above list is intended to provide examples and guidance and is not intended to be exhaustive or limit the scope of the invention defined in the appended claims.

Isostatic Pressing

The term "isostatic pressing" refers to the powder compaction method involving applying pressure from multiple directions through a liquid or gaseous medium surrounding the compacted part.

The phrase "cold isostatic pressing" (CIP) refers to isostatic pressing that is conducted at room temperature. The CIP method can include a flexible (commonly polyurethane) mold immersed in a pressurized liquid medium (commonly water) in the cold isostatic pressing method. There are two types of cold isostatic pressing: wet bag and dry bag. In the wet bag method the mold is removed and refilled after each pressure cycle. This method is suitable for compaction of large and complicated parts. In the dry bag method the mold is an integral part of the vessel. The dry bag method is used for compaction of simpler and smaller parts. The cold isostatic pressing (CIP) method has the following advantages as compared to the die cold pressing method: better uniformity of compaction, and more complex forms (for example long thin-walled tubes) may be compacted.

The phrase "warm isostatic pressing" (WIP) refers to isostatic pressing that is conducted at increased temperature. The WIP may include as a medium a gas (Nitrogen or Argon). Although Hot isostatic pressing (HIP) commonly uses increased work pressures, between 15,000 psi to 44,000 psi (100 MPa to 300 MPa), the present invention does not contemplated the use of increased pressures in the warm isostatic pressing (WIP) step. Further, warm isostatic method (WIP) causes consolidation of powder particles, healing voids and pores. The part shrinks and densifies, forming sound high strength structure. WIP, as used herein, will include the use of a mold.

Example Articles

The present invention contemplate the production of virtually any article or part that is currently made using sintering technology.

Alumina Articles

Examples include aluminum oxide articles that are used for manufacturing insulators, capacitors, resistors, furnace tubes, sealing refractory parts, foundry shapes, wear pads, thermocouple protection tubes, cutting tools, polishing/grinding powders, ballistic armor, laboratory equipment, bio-ceramic parts for orthopedic prosthetic replacements, dental crowns, bridges and other dental appliances, and bearings.

Magnesia Articles

Magnesia articles are used for manufacturing high temperature crucibles, thermocouple tubes, heating elements, foam ceramic filters for molten metal, linsulators, steel making refractories, kiln furniture.

Zirconia Articles

Zirconia articles are used for manufacturing extrusion dies, powder compacting dies, cutting tools, balls and seats for ball valves, thread and wire guides, pump seals, impellers and shaft guides, engine parts, oxygen sensors, fuel cells membranes, high temperature heaters for electric furnaces, bearings (e.g., bearings for submersible pumps).

Aluminum titanate Articles

Aluminum Titanate articles are used for manufacturing crucibles, launders, nozzles, riser tubes, pouring spouts and thermocouples for non-ferrous metallurgy, portliner and cylinder liners in automotive engines, master moulds in the glass industry, spacing rings of catalytic converters.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Having described embodiments for the invention herein, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

The invention claimed is:

1. A process for producing a sintered powder manufactured item, comprising the steps:
   STEP 1—preparing a sacrificial powder mold of a manufactured item, the sacrificial powder mold made using 3D printing and the sacrificial powder of the sacrificial powder mold consisting of a high-temperature sintering powder and a swellable binder to create a self-destructible sacrificial powder mold when sintered;
   STEP 2—loading a powder sintering material into the sacrificial powder mold to create a powder-mold assembly, wherein the powder sintering material is substantially free of binder;
   STEP 3—applying isostatic pressure to the powder-mold assembly;
   STEP 4—sintering of the powder-mold assembly; and
   STEP 5—obtaining a sintered-powder cast manufactured item from the self-destructed sintered sacrificial powder mold.

2. The process of claim 1, wherein the powder sintering material of STEP 2 is metal or ceramic.

3. The process of claim 1, wherein the isostatic pressure of STEP 3 is at least 400 MPa.

4. The process of claim 1, wherein the sintering of STEP 3 is at 1400 degrees Celsius for 4 hours under a heating rate of 3 degrees Celsius/minute.

5. The process of claim 1, wherein the loading of STEP 2 includes a preliminary step of coating the sacrificial powder mold with a graphite spray.

6. The process of claim 1, wherein the high-temperature sintering powder of STEP 1 is alumina, and the swellable binder of STEP 1 is selected from the group consisting of a polysaccharide, a mono-saccharide, a di-saccharide, a tri-saccharide, a starch, a carbohydrate, a saccharide derivative, and a mixtures and a combination thereof.

7. A method consisting of:
   STEP 1—preparing a sacrificial powder mold of a dental crown, the sacrificial powder mold made using 3D printing and the sacrificial powder of the sacrificial powder mold consisting of a high-temperature alumina sintering powder and at least one swellable binder to create a self-destructible sacrificial powder mold when sintered;
   STEP 2—loading a zirconia powder sintering material into the sacrificial powder mold to create a powder mold assembly, wherein the powder sintering material is substantially free of binder;
   STEP 3—applying isostatic pressure to the powder-mold assembly;
   STEP 4—sintering of the powder-mold assembly in a tube furnace; and
   STEP 5—obtaining a sintered-powder cast zirconia dental crown from the self-destructed sintered sacrificial powder mold, wherein the relative density of the dental crown is about 99.42%.

8. The process of claim 7, wherein the powder sintering material of STEP 2 is metal or ceramic.

9. The process of claim 7, wherein the isostatic pressure of STEP 3 is at least 400 MPa.

10. The process of claim 7, wherein the sintering of STEP 3 is at 1400 degrees Celsius for 4 hours under a heating rate of 3 degrees Celsius/minute.

11. The process of claim 7, wherein the loading of STEP 2 includes a preliminary step of coating the sacrificial powder mold with a graphite spray.

12. The process of claim 7, wherein the high-temperature sintering powder of STEP 1 is alumina, and the swellable binder of STEP 1 is selected from the group consisting of a polysaccharide, a mono-saccharide, a di-saccharide, a tri-saccharide, a starch, a carbohydrate, a saccharide derivative, and a mixtures and a combination thereof.

13. The method of claim 7, wherein the zirconia powder sintering material is a 3 mol % yttria-stabilized zirconia powder.

14. The method of claim 7, wherein the sacrificial powder mold of STEP 1 consists of 74% alumina, 13% powdered sugar and 13% maltodextrin.

* * * * *